US010876972B2

(12) United States Patent
Yang

(10) Patent No.: US 10,876,972 B2
(45) Date of Patent: Dec. 29, 2020

(54) FULL SCALE RAMAN IMAGING FOR EARLY CARIES DETECTION

(71) Applicant: Shan Yang, Madison, MS (US)

(72) Inventor: Shan Yang, Madison, MS (US)

(73) Assignee: Jackson State University, Jackson, MS (US)

(*) Notice: Subject to any disclaimer, the term of this patent is extended or adjusted under 35 U.S.C. 154(b) by 0 days.

(21) Appl. No.: 16/426,959

(22) Filed: May 30, 2019

(65) Prior Publication Data
US 2019/0369025 A1    Dec. 5, 2019

Related U.S. Application Data

(60) Provisional application No. 62/677,746, filed on May 30, 2018.

(51) Int. Cl.

| | | |
|---|---|---|
| *G01J 3/44* | (2006.01) | |
| *G01N 21/65* | (2006.01) | |
| *G01J 3/10* | (2006.01) | |
| *G01J 3/02* | (2006.01) | |
| *G01J 3/28* | (2006.01) | |

(52) U.S. Cl.
CPC .......... *G01N 21/65* (2013.01); *G01J 3/0224* (2013.01); *G01J 3/10* (2013.01); *G01J 3/2823* (2013.01); *G01J 3/44* (2013.01); *G01N 2201/06113* (2013.01)

(58) Field of Classification Search
CPC . G01N 21/65; G01N 21/64; G01J 3/10; G01J 3/44; G01J 3/36; G01J 3/28; G01J 3/02
See application file for complete search history.

(56) References Cited

U.S. PATENT DOCUMENTS

| | | | |
|---|---|---|---|
| 2011/0310395 A1* | 12/2011 | Tsai ................... | G01B 9/02091 356/479 |
| 2015/0204789 A1 | 7/2015 | Akkus et al. | |
| 2016/0131885 A1* | 5/2016 | Nakayama ........ | G01N 21/6428 250/458.1 |

(Continued)

OTHER PUBLICATIONS

Dye BA, Thornton-Evans G, Li X, Iafolla TJ., "Dental caries and tooth loss in adults in the United States, 2011-2012. NCHS data brief, No. 197.Hyattsville, MD: National Center for Health Statistics. 2015.," https://www.cdc.gov/nchs/products/databriefs/db197.htm.

(Continued)

*Primary Examiner* — Abdullahi Nur

(74) *Attorney, Agent, or Firm* — Butler Snow LLP

(57) ABSTRACT

An improved hyperspectral Raman imaging system and device that obtains full scale Raman images from a sample surface in seconds, wherein the dichromic mirror is located between the objective lens and sample surface. The laser is delivered to the sample surface and the Raman image is collected and transmitted through optic fiber to a camera after filtration. By delivering the laser to the sample without going through the objective lens, a high-power laser can safely illuminate the full field of view of the objective lens, allowing for safe Raman imaging within seconds. This fast and safe Raman imaging system can be used for, among other applications, the early detection of dental caries in practical settings.

9 Claims, 4 Drawing Sheets

(56) References Cited

U.S. PATENT DOCUMENTS

2017/0108688 A1* 4/2017 Chalmers .............. G02B 21/361
2018/0120432 A1* 5/2018 Misra ...................... G01S 17/10

OTHER PUBLICATIONS

Dye BA, Thornton-Evans G, Li X, Iafolla TJ., "Dental caries and sealant prevalence in children and adolescents in the United States, 2011-2012. NCHS data brief, No. 191. Hyattsville, MD: National Center for Health Statistics.," (2015).

A. I. Ismail, "Visual and Visuo-tactile Detection of Dental Caries," J. Dent. Res. 83(1_suppl), 56-66 (2004).

A. C. Ko, M. Hewko, M. G. Sowa, C. C. Dong, B. Cleghorn, and L.-P. Choo-Smith, "Early dental caries detection using a fibre-optic coupled polarization-resolved Raman spectroscopic system," Opt. Express 16(9), 6274 (2008).

B. Angmar-Månsson and J. J. Ten Bosch, "Optical Methods for the Detection and Quantification of Caries," Adv. Dent. Res. 1(1), 14-20 (1987).

B. T. Amaechi and S. M. Higham, "Quantitative light-induced fluorescence: A potential tool for general dental assessment," J. Biomed. Opt. 7(1), 7 (2002).

J. D. Bader and D. A. Shugars, "A systematic review of the performance of a laser fluorescence device for detecting caries;" J. Am. Dent. Assoc. 135(10), 1413-1426 (2004).

S. Yang, B. Li, A. Akkus, O. Akkus, and L. Lang, "Wide-field Raman imaging of dental lesions," The Analyst 139(12), 3107 (2014).

\* cited by examiner

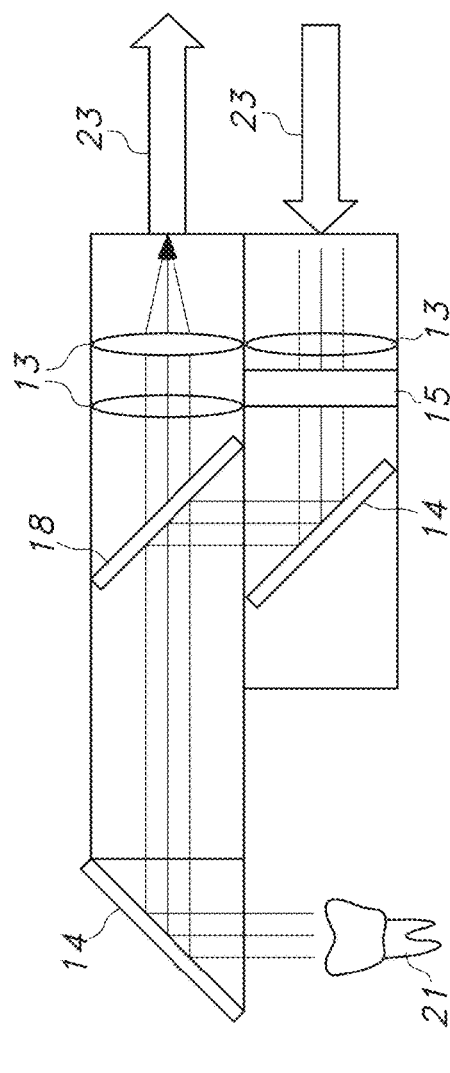
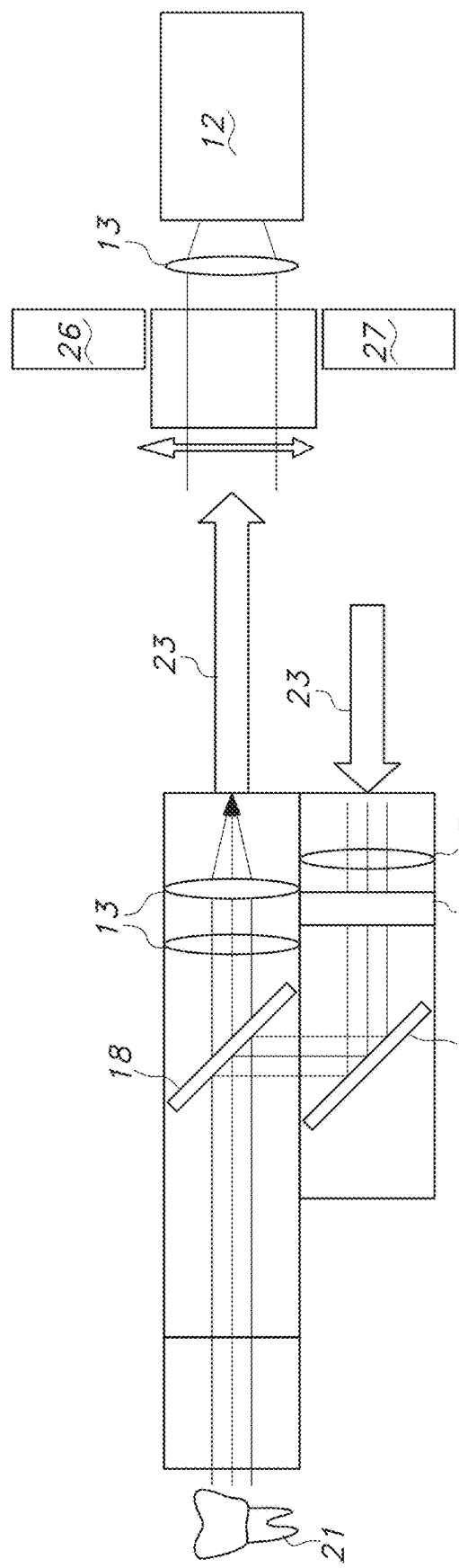
FIG. 2A
FIG. 2B

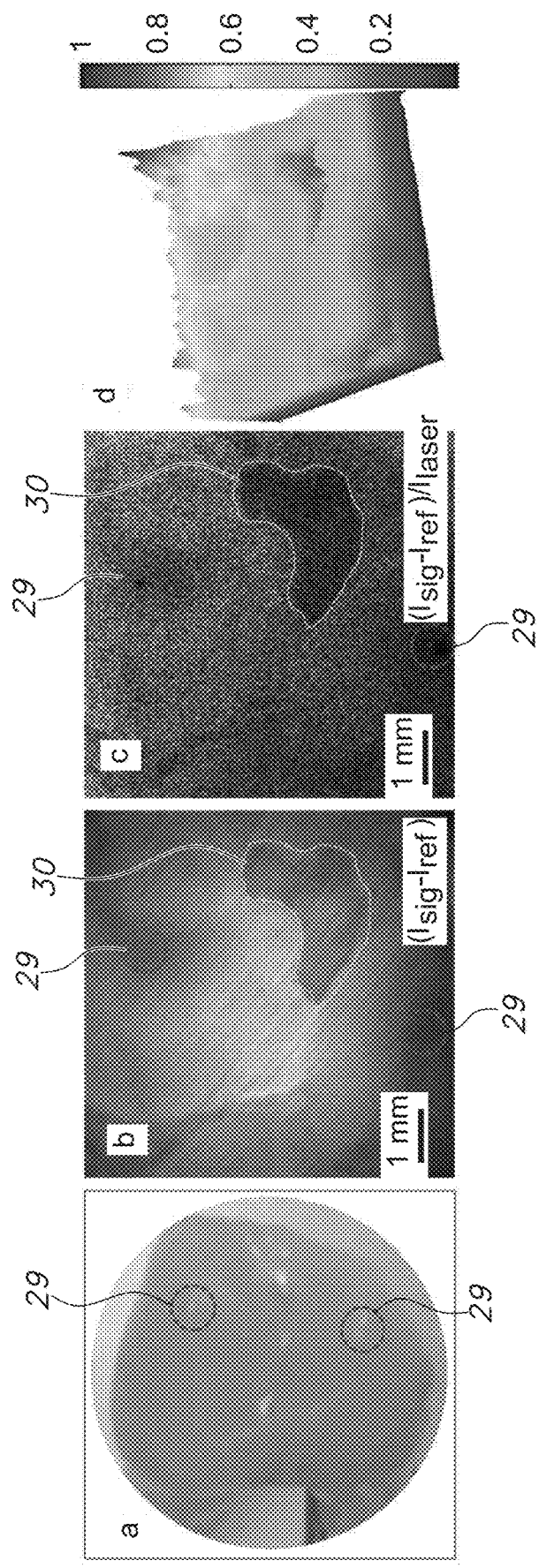

FULL SCALE RAMAN IMAGING FOR EARLY CARIES DETECTION

CROSS-REFERENCE TO RELATED APPLICATIONS

This application claims priority to U.S. Provisional Application No. 62/677,746 filed on May 30, 2018, the contents of which are incorporated herein by reference in its entirety.

STATEMENT REGARDING FEDERALLY SPONSORED RESEARCH OR DEVELOPMENT

This invention was made with Government support under Grant DE027240 awarded by the National Institutes of Health. The Government has certain rights in the invention.

FIELD OF THE INVENTION

The present invention is related to detection of dental caries. Specifically, the invention is related to an improved Raman imaging system for early detection of dental caries via Raman imaging.

BACKGROUND

While the prevalence of dental caries has declined compared to five-decades ago, there is a need to improve the methods currently employed for caries prevention. The most effective way of stopping dental caries is to detect the decay at early stage, when decays may be stopped or even reversed through noninvasive treatments by using fluoride, ozone, or MI paste. However, early dental caries are often not visible to the eyes and, thus, overlooked by dentists during regular dental examination. Once decays are visible to eyes, explorer, or radioactive imaging (e.g., x-rays), invasive fillings are typically required to stop the decays. Fillings may fail over time and more advanced repairing is eventually needed.

Tremendous efforts have been invested on the development of optics-based spectroscopy and imaging technologies for early caries detection because of their unique advantages, such as, non-invasive and noncontaminant measurements and real-time analysis. Fluorescence based technology is the most popular among all optical approaches for early caries detection, which is evidenced by several commercial products: KaVo DIAGNOdent, Spectra from Air Techniques, Caries I.D, etc. The fluorescence-based detection devices have high sensitivity for caries detection as the fluorescence level of decayed enamel is higher than the level of normal enamel. However, because many other objects in the oral environment also produces high fluorescence compared to normal enamel, fluorescence-based devices suffer from a low specificity or high false alarm rate.

Raman spectroscopy has been shown to be effective to differentiate early onset of caries on enamel from healthy enamel. However, Raman spectroscopy and imaging has not been implemented in clinical application due to the lengthy examination time. In the current manner of Raman imaging, the laser is delivered through an objective lens to the sample, then the same lens is used to collect Raman signals in the backscattering configuration. Because the objective lens always converges the laser, the laser is only illuminating the central portion of the field of view of the objective lens. The effect of the converging limits the power of the laser because high intensity laser will damage the tooth.

Raman spectroscopy may detect the change of mineral (the most abound content of enamel) concentration in enamel due to early decay. Early study shows decay analysis with Raman spectroscopy yields >95% sensitivity and >95% specificity. Therefore, Raman spectroscopy is promising for early dental decay detection. Fiber based Raman probes focus laser light tightly to tiny spots that are highly possible to misplace with small sized early decays. Thus, an expeditious imaging of tooth surface via Raman spectroscopy is needed in the art to facilitate clinical application.

BRIEF DESCRIPTION OF THE DRAWINGS

Further advantages of the invention will become apparent by reference to the detailed description of preferred embodiments when considered in conjunction with the drawings:

FIG. 1A depicts a schematic view of one embodiment of the components and layout of the Raman imaging system. FIG. 1B depicts a typical Raman spectrum of teeth when the band-pass filter is adjusted to center at 960 cm$^{-1}$, 880 cm$^{-1}$ and raw spectrum.

FIGS. 2A-2B depict a schematic view of one embodiment of the components and layout for the full field of view of the Raman imaging system. Individually, FIG. 2A depicts a schematic view of an embodiment of the components and layout for the full field of view of the Raman imaging system of a top of a tooth. FIG. 2B depicts a schematic view of an embodiment of the components and layout for the full field of view of the Raman imaging system of a side of a tooth.

FIG. 3A depicts a photograph of a tooth lesion. FIG. 3B depicts a full-scale image covering the lesion with the band-pass filter tuned to Raman signal peak. FIG. 3C depicts a full-scale image covering the lesion with the band-pass filter tuned to a fluorescence reference. FIG. 3D depicts the fluorescence subtracted image before laser intensity correction.

FIG. 4A-4D depict views of a tooth lesion. Individually, FIG. 4A depicts a photograph of a tooth lesion. FIG. 4B depicts a full-scale fluorescence subtracted Raman image of the top surface of the tooth before laser intensity correction. FIG. 4C depicts a full-scale fluorescence subtracted Raman image of the top surface of the tooth after laser intensity correction. FIG. 4D depicts the laser intensity corrected Raman image replotted in 3D format for additional viewpoints.

SUMMARY OF THE INVENTION

Figure 1A:
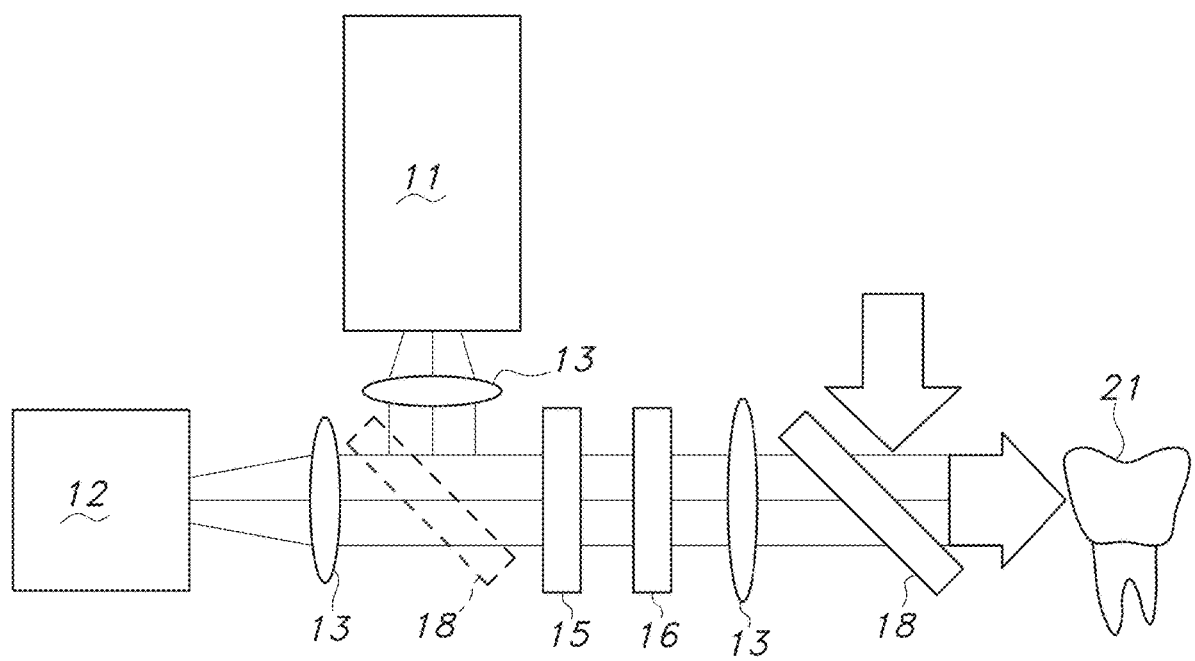
FIGS. 1A-1B depict an embodiment of the Raman imaging system. Individually.

Raman imaging systems known in the art detect dental caries earlier but are not implemented in clinical practice due to the excessive time necessary to conduct the imaging process. The presently disclosed invention is a macroscopic hyperspectral Raman imaging system method and device capable of capturing full scale images of tooth surfaces comprising a camera, band-pass filter, laser, a plurality of lenses, and a dichroic mirror, wherein the dichroic mirror is placed between the objective lens and the tooth sample surface. Placing the dichroic mirror between the objective lens and tooth sample surface ensures the laser beams are delivered to the tooth sample directly without being focused by the objective lens. Thus, the illumination area is the same size as the beam diameter, which can be adjusted to fully cover the tooth surface and decreases the amount of time necessary to obtain Raman images covering complete tooth surfaces. The decreased amount of time necessary to conduct the dental caries detection by the Raman imaging system taught herein allows for clinical application of Raman imaging, which will result in increased early detection of dental caries.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Raman imaging systems known in the art require image acquisition times that prevent use of the systems in clinical settings. The system disclosed herein modifies the current systems and teaches a Raman imaging system 10 that obtains Raman images covering complete tooth surfaces in the order of a few seconds. Thus, this system clears the major road block preventing the application of Raman imaging on early caries detection in dental medicine.

The invention allows for early caries detection and screening in the dental field, but the full field of view Raman imaging system can also be applied to any other material where 2D spatial information is desired. For non-biological or non-medical applications, the full field of view imaging can be used for many material analyses given high laser power and enough integration time up to 30 minutes.

The presently disclosed invention teaches a hyperspectral Raman imaging system 10 method and device capable of capturing full scale Raman images of a surface in seconds comprising a 2-D camera 12, band-pass filter 15, a laser 19, a plurality of lenses 13, and a dichroic mirror 18, wherein the dichroic mirror 18 is placed between the objective lens 13 and the tooth or other sample surface 21.

Raman images taken from the camera 12 are based on the concentration distribution of mineral, which is the most abundant content of enamel. Mineral is Raman active, and the intensity of its fingerprint Raman signal varies with its concentration. Raman images are constructed based on the signal intensities of an active Raman bond-phosphate symmetric stretch bond of mineral, which appears at ~960 cm-1 in Raman spectrum. The mineral Raman signal is isolated from other Raman signals by a narrow band-pass filter 15, and the image is directly captured by a 2D camera 12.

This invention modifies the configuration of a typical Raman imaging system by placing a dichroic mirror 18 between the objective lens 13 and the sample surface 21. The modification ensures the laser beam 20 of the laser 19 is delivered to the sample surface 21 without going through the objective lens 13. Thus, the laser 19 is not focused to the central field of view region. Instead, the laser beam 20 can be adjusted to illuminate the full field of view of the objective lens 13, which is contemplated to be 1-20 mm in diameter. Because the laser beam 20 is spread out over the very large area, the high-power laser 19 can be employed for fast imaging, while the laser 19 intensity remains at a safe range.

The major benefit of this configuration is that the illumination beams 20 are delivered to the sample directly without being focused by the objective lens 13. Thus, the illumination area is the same size as the laser beam 20 diameter, which can be adjusted to fully cover the tooth surface 21. This full field of view is at the scale of the sample surface 21 dimension. The Raman imaging method enables acquisition of Raman images from a tooth sample surface 21 at a time scale that is practical for clinical application. The full field of view Raman imaging is realized via delivering a non-converged laser beam 20 to the sample surface 21. As discussed above, the sample surface 21 may be that of a tooth or other spatial 2-D orientation. Thus, it is contemplated that the top or side of a tooth may be obtained by the Raman imaging system taught herein, as shown in FIGS. 2A-2B.

In an embodiment of the system, light is emitted from the laser 19 and routed through the dichroic mirror 18 and is reflected then delivered to the sample surface 21 without focus, as shown in FIG. 1A. The signal comes back from the sample surface 21 and through the dichroic mirror 18 and is collected from the objective lens 13 to the 2-D camera 12. The 2-D camera 12 will not directly recognize the signal, so another lens 13 is utilized to make a focal point of the scattered light.

In an embodiment of the system, a handheld or otherwise mobile probe 22 is utilized that can be carried to patients in a clinical or other practical setting. The probe 22 is connected to the laser 19 and 2-D camera 12 via optical fiber or fiber bundle 23 and used to deliver the Raman images to the camera 12 through the optical fiber(s) 23, as shown in FIGS. 2A-2B. Specifically, the laser beam 20 is delivered to the tooth sample surface 21, and the Raman image is then collected with the objective lens 17 and transmitted through a single optical fiber or fiber bundle 23 to the 2-D camera 12, after being filtered through a narrow band-pass filter or filters 15.

An embodiment of the laser 19 includes a Ti:sapphire laser or any other laser that can provide minimum 500 mW laser light with spectral bandwidth less than 1 nm and a power range from 0.5-30 watts. For instance, an excitation laser at 730-850 nm range may be used, and the laser can be collimated or slightly diverging.

In an embodiment of the objective lens 13, Raman images are acquired via an anti-reflection achromatic lens (f=50-250 mm), whose long focal distance allows placing the dichroic mirror 18 between the achromatic lens 13 and the tooth surface sample 21. Thus, the illumination area is the same size as the laser beam 20 diameter, which is adjusted to be approximately 1 cm in diameter on the tooth sample surface 21, as shown in FIG. 2. In addition to achromatic lenses, other objective lenses 13, including, but not limited to, collimating lenses and imaging lenses that adjust the laser beam 20 are contemplated herein.

In an embodiment of the system, cameras 12 with 1024 pixels×1024 pixels or 2048 pixels×2048 pixels are used. A f=200-500 mm lens can be used to focus the images on the 2-D camera 12. Charge-coupled devices (CCD) cameras are also contemplated herein. The 2-D cameras 12 should be cooled to −15 Celsius or more to reduce noise and prevent signal interference.

Figure 1B:
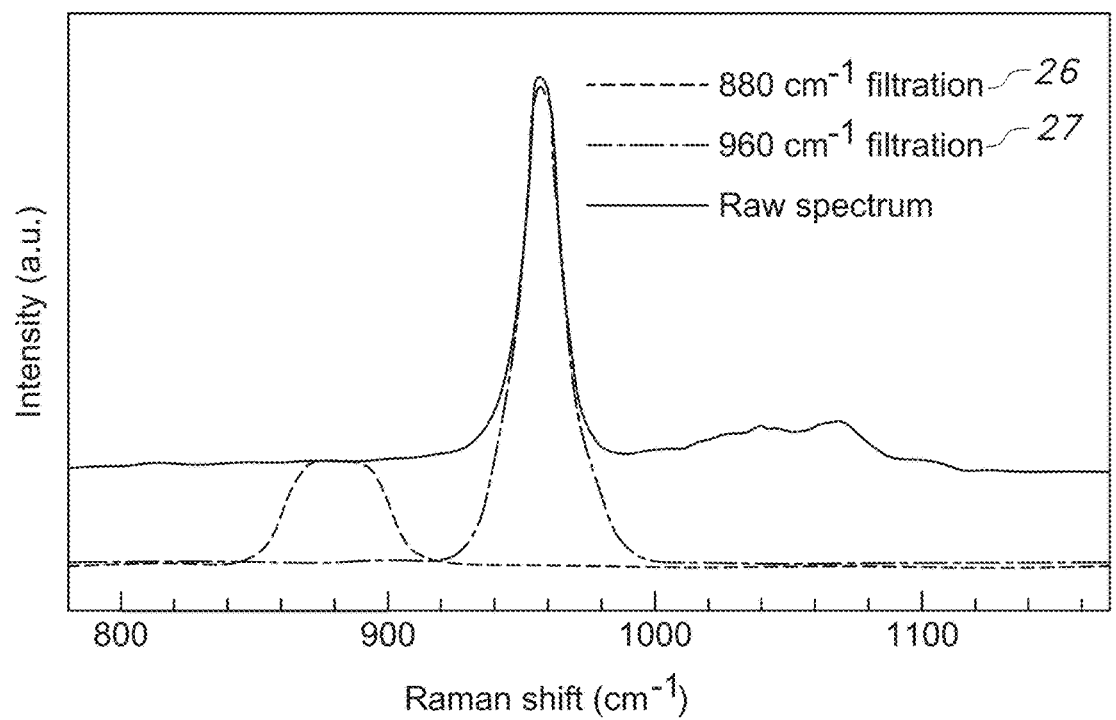

In an embodiment of the system, an edge filter 16 may be inserted to reject the Rayleigh scattering from the tooth surface sample 21, and one or a pair of narrow band-pass filters 15 is used to pick up the 960 cm$^{-1}$ mineral Raman signal associated with the mineral phase, as shown in FIG. 1B. The narrow band-pass filters 15 are switchable between $I_{880}$ 26 and $I_{960}$ 27. The second acquisition at the valley of the mineral peak at ~880 cm$^{-1}$ (by slightly rotating the narrow band pass filter 15) is conducted to obtain the background fluorescence, as shown in FIG. 1B. Subtraction of the two acquisitions results in a 2D image displaying the distribution of the mineral intensity. Integration time of 5-10 seconds may be used for the acquisition of Raman images.

In an embodiment of the system, while an objective lens 13 is used to collect Raman image, which is then focused to an optical fiber or fiber bundle 23 and then delivered to the camera 12, a laser intensity distribution image is also acquired and then used to calibrate the fluorescence subtracted Raman image by division, as shown in FIGS. 4A-4C. This step corrects the non-uniformity of laser distribution due to optical distortion and sample surface variation, which enhances the contrast between enamel and dentin. Finally, the laser intensity calibrated mineral distribution image may be normalized, blurred with Gaussian filter, and replotted in the colored 3D format for additional viewpoints.

In an embodiment of the system, the Raman signal may be routed to a Raman spectrometer 11 to verify the complete removal of the Rayleigh scattering. The Raman signal may also be routed to a Raman spectrometer 11 to verify the correct selection of the Raman peaks before image acquisition. However, a Raman spectrometer 11 is not required in a well calibrated system.

EXAMPLES

Raman images were constructed based on the integrated Raman signal relating to the phosphate symmetric stretch bond of mineral, which appears at ~960 cm$^{-1}$ 18 in the Raman spectrum. The Raman images were acquired via an anti-reflection achromatic lens (f=150 mm) 13, whose long focal distance allowed placing the dichroic mirror 18 between the lens 13 and the sample 21. Thus, the illumination area was the same size as the laser beam 20 diameter, which had been adjusted to be approximately 1 cm in diameter on the sample surface. A high power tunable Ti:Sapphire laser operating at 785 nm was used as the laser 19 and a deep-cooled NIR enhanced 2D camera 12 was used to capture Raman images, as shown in FIG. 1A.

An edge filter 16 at 785 nm was inserted to reject the Rayleigh scattering from the sample, and one or a pair of narrow band pass filter 15 were used to pick up the 960 cm$^{-1}$ 26 mineral Raman signal associated with the mineral phase, as shown in FIG. 1B. The second acquisition at the valley of the mineral peak at ~880 cm$^{-1}$ 26 (by slightly rotating the narrow band pass filter 15) was conducted to obtain the background fluorescence, as shown in FIG. 1B. Subtraction of the two acquisitions resulted in a 2-D image displaying the distribution of the mineral intensity. Integration time of 5-10 seconds may be used for the acquisition of Raman images.

The laser power was set in the range of 1-2 watts, which is well below the damage threshold of tooth. For a camera 12 that has 1024×1024 pixels with pixel size of 13 μm, the full-scale imaging size (6.66 mm×6.66 mm) was half of the chip size when an f=300 mm lens was used to focus the images onto the 2D camera 12.

Figure 3A:
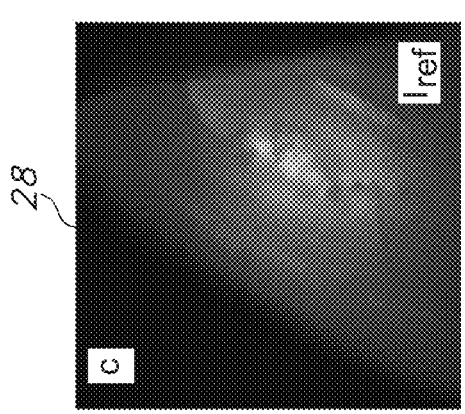
FIGS. 3A-3D depict views of a tooth lesion. Individually.
Figure 3B:
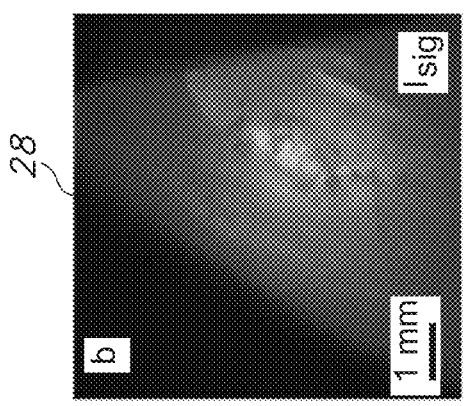
Figure 3C:
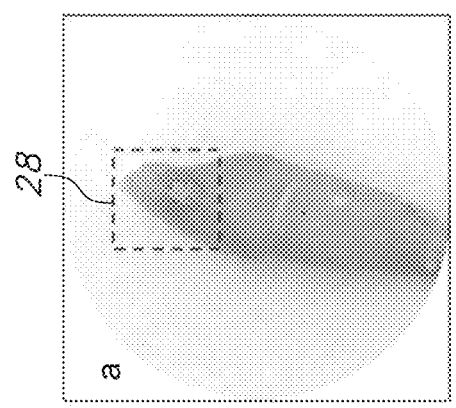
Figure 3D:
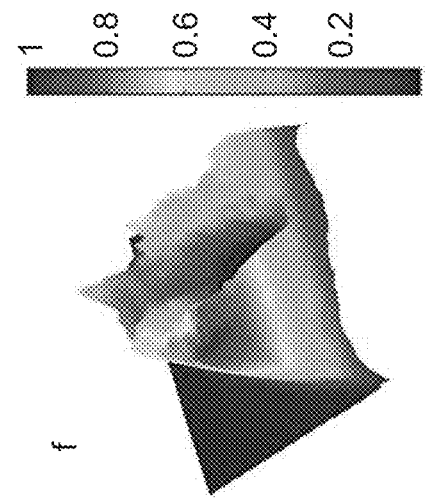
Figure 3E:
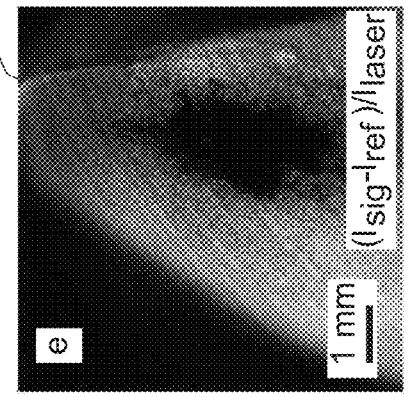
FIG. 3E depicts the fluorescence subtracted image after laser intensity correction.
Figure 3F:
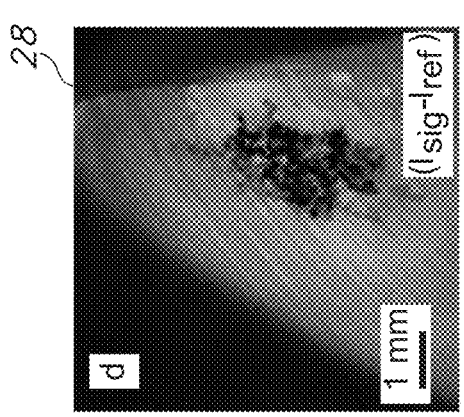
FIG. 3F depicts the laser intensity corrected Raman image replotted in 3D format for additional viewpoints.

The imaging system 10 was used to test on a human tooth, an incisor, which had developed an over 1 mm white lesion 28, as depicted in FIG. 3A, on one of its side surfaces. The power of the illumination laser light 20 was kept the same at 600 mW on the sample surface 21, and the integration time of the camera 12 was set at 30 seconds, which is a longer integration time than clinical practice for better illustration. White lesions 28 visible to naked eyes are shown in a picture taken by a cell phone camera 12 in FIG. 3A. FIGS. 3B-3C depict the full-scale images when the tunable filter was respectively set for the Raman signal and fluorescence reference correspondingly and normalized by the maximum shown in FIG. 3B. The lesion was confirmed by fluorescence subtracted Raman image, as depicted in FIG. 3D. The laser intensity corrected Raman image demonstrates the improved contrast between normal and caries regions in FIG. 3E.

The imaging system 10 is able to analyze teeth that do not have a noticeable lesion 26, which could easily be misdiagnosed as a healthy tooth under visual examination, as shown in FIG. 4A. The laser power for this tooth was increased to be 800 mW while the integration time was set at 10 seconds. The Raman images, before (FIG. 4B) and after (FIG. 4C) laser intensity correction, indicated that the mineral intensity 30 in the marked region (dashed lines) was significantly lower than the rest of the tooth, suggesting a caries was probably forming in this area. In the meantime, cusp tips 29 were observed showing lower mineral intensity, as depicted in FIGS. 4A-4C, than surroundings, which could indicate increased occlusal tooth wear and possible dentin exposure. The small region on the top right corner had the highest mineral intensity.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all sub-ranges and individual values are intended to be encompassed. This invention is not to be limited by the embodiments disclosed, including any shown in the drawings or exemplified in the specification, which are given by way of example and not of limitation. Additionally, it should be understood that the various embodiments of the knotless anchor assembly described herein contain optional features that can be individually or together applied to any other embodiment shown or contemplated here to be mixed and matched with the features of that device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

I claim:

1. An improved Raman imaging system for obtaining images from a sample surface in seconds comprising:
   a. a laser;
   b. a 2-D camera;
   c. A band-pass filter;
   d. a plurality of lenses;
   e. a sample surface;
   f. and a dichroic mirror, wherein the dichroic mirror is placed between an objective lens and the sample surface, further wherein the laser is delivered to the sample surface without going through the objective lens.

2. The Raman imaging system of claim 1 wherein a probe is connected to the laser and 2-D camera via optical fiber, further wherein the probe delivers Raman images to the camera through optical fiber.

3. The system of claim 1 further comprising an edge pass filter.

4. The system of claim 1 wherein the objective lens is an imaging lens.

5. The system of claim 1 wherein the objective lens is a collimating lens.

6. The system of claim 1 wherein the objective lens is an achromatic lens.

7. A device for obtaining Raman images from a sample surface comprising: a. a probe connected to a laser and a 2-D camera via optical fiber, wherein the probe delivers Raman images to the camera through optical fiber; b. a band-pass filter; c. a plurality of lenses; d. a sample surface; and e. a dichroic mirror, wherein the dichroic mirror is placed between an objective lens and the sample surface, wherein the laser is delivered to the sample surface without going through the objective lens.

8. The probe of claim 7 wherein the probe is handheld.

9. An improved method of obtaining Raman images of a sample surface comprising:
   a. emitting light from a laser through a dichroic mirror placed between the objective lens and the sample surface;
   b. reflecting and delivering the light to a sample surface;
   c. transmitting the signal from the sample surface and through a narrow band-pass filter and the dichroic mirror;
   d. collecting the sample from an objective lens to a 2-D camera; and
   e. focusing the scattering light via an objective lens, wherein the laser is delivered to the sample surface without going through the objective lens.

* * * * *